(12) United States Patent
Kwon et al.

(10) Patent No.: US 8,716,288 B2
(45) Date of Patent: May 6, 2014

(54) COMPOSITION COMPRISING BENPROPERINE DERIVATIVES AS ACTIVE INGREDIENTS FOR PREVENTING AND TREATING ANGIOGENESIS-RELATED DISEASES

(71) Applicants: Byoung Mog Kwon, Daejeon (KR); Dong Cho Han, Daejeon (KR); Dae Seop Shin, Daejeon (KR); Young Min Han, Daejeon (KR)

(72) Inventors: Byoung Mog Kwon, Daejeon (KR); Dong Cho Han, Daejeon (KR); Dae Seop Shin, Daejeon (KR); Young Min Han, Daejeon (KR)

(73) Assignee: Korea Research Institute of Bioscience and Biotechnology, Daejon (KR)

( * ) Notice: Subject to any disclaimer, the term of this patent is extended or adjusted under 35 U.S.C. 154(b) by 0 days.

(21) Appl. No.: 13/891,837

(22) Filed: May 10, 2013

(65) Prior Publication Data

US 2013/0245068 A1    Sep. 19, 2013

Related U.S. Application Data

(63) Continuation-in-part of application No. PCT/KR2011/008625, filed on Nov. 11, 2011.

(30) Foreign Application Priority Data

Nov. 11, 2010   (KR) .......................... 10-2010-0112343

(51) Int. Cl.
   A61K 31/5377   (2006.01)
(52) U.S. Cl.
   USPC ..................................................... 514/237.2
(58) Field of Classification Search
   None
   See application file for complete search history.

(56) References Cited

U.S. PATENT DOCUMENTS

| 2009/0203763 A1 | 8/2009 | Gant |
| 2010/0087455 A1 | 4/2010 | Gant |
| 2010/0226943 A1 | 9/2010 | Brennan et al. |

FOREIGN PATENT DOCUMENTS

WO   WO 2009/018280 A2   2/2009

OTHER PUBLICATIONS

Du, ZM., et al., "Enantioselective pharmacokinetics of penproperine in healthy volunteers", Yao Xue Xue Bao. Dec. 2000; 35 (12):909-12.(Abstract in English provided to applicant: translation from Chinese for full article to be sent later).*
Written Opinion of the International Searching Authority mailed Jun. 29, 2012 in connection with PCT International Application No. PCT/KR2011/008625, filed Nov. 11, 2011.
International Preliminary Report on Patentability Chapter I issued May 14, 2013 in connection with PCT International Application No. PCT/KR2011/008625, filed Nov. 11, 2011.
Li et al. (2006). Identification and quantitative determination of benproperine metabolites in human plasma and urine by liquid chromatography-tandem mass spectrometry. Journal of Chromatography B, 830, 71-80.
International Search Report, mailed Jun. 29, 2012 in connection with PCT International Application No. PCT/KR2011/008625, filed Nov. 11, 2011.

* cited by examiner

*Primary Examiner* — San Ming Hui
*Assistant Examiner* — Jeanmarie Calvillo
(74) *Attorney, Agent, or Firm* — John P. White; Cooper & Dunham LLP (57) ABSTRACT

The present invention relates to a novel pharmaceutical composition of benproperine derivatives for preventing and treating angiogenesis-related diseases. The benproperine derivatives and pharmaceutically acceptable salts thereof according to the present invention inhibit cancer cell migration and the angiogenesis of vascular endothelial cells, and therefore can be effectively used not only as an anticancer agent, but also as an agent for preventing and treating diseases caused by abnormal angiogenesis, such as diabetic retinopathy and corneal transplant rejection.

16 Claims, 6 Drawing Sheets

0.1% DMSO

Formula 2

Formula 3

Formula 4

COMPOSITION COMPRISING BENPROPERINE DERIVATIVES AS ACTIVE INGREDIENTS FOR PREVENTING AND TREATING ANGIOGENESIS-RELATED DISEASES

CROSS-REFERENCE TO RELATED APPLICATIONS

This application is a continuation-in-part of PCT International Application No. PCT/KR2011/008625, filed Nov. 11, 2011, and claims priority of Korean Patent Application No. 10-2010-0112343, filed Nov. 11, 2010, the contents of each of which are hereby incorporated by reference in its entirety.

BACKGROUND OF THE INVENTION

1. Field of the Invention

The present invention relates to a novel pharmaceutical composition for preventing or treating angiogenesis-related diseases, comprising benproperine derivatives represented by Formula 1 or pharmaceutically acceptable salts thereof. The benproperine derivatives and pharmaceutically acceptable salts thereof according to the present invention can effectively inhibit the metastasis of cancer by inhibiting cancer cell migration and the angiogenesis, and therefore can be valuably used not only as an anticancer agent, but also as an agent for preventing and treating diseases caused by abnormal angiogenesis.

[Formula 1]

Wherein, $R_1$ and $R_2$ are independently hydrogen or hydroxyl.

2. Description of the Related Art

Angiogenesis is the biological process by which new blood vessels are supplied in the tissue or organ and specifically means that new capillaries are created from existing microvessels, which is the fundamental process by which blood vessels are generated in the body after growth. Physiological angiogenesis which is normally observed in the human body occurs only under very limited circumstances, such as embryonic and fetal development, maturation of uterus, proliferation of placenta, formation of corpus luteum and wound healing, and even in this period, is very strictly controlled and stops once required characteristic is achieved. New angiogenesis is strictly controlled by angiogenesis regulatory factor, and the angiogenic phenotype has been reported to be switched by the overall balance between up-regulation of angiogenesis stimulatory factor and down-regulation of angiogenesis inhibitory factor (Folkman, J. (1995) J. Nature Med. 1: 27-31).

The process by which new blood vessels are generated, although very complex elaborate, can be summarized as follows. First, when the stimulus for angiogenesis is delivered to existing blood vessels, blood vessels are distended and membrane permeability increases. Second, fibrin comes out of the vessels through the distant blood vessels are deposited on the perivascular cytoplasmic matrix. Third, the enzyme necessary to decompose the basal membrane of existing blood vessels is activated which leads to the destruction of basal membrane, through which endothelial cells exit from the vessel followed by multiplying in the surrounding cell substrates and moving around. Finally, the new blood vessels are created through the vasculature of aligned endothelial cells (Risau, W. (1997) Nature 386: 671-674).

Angiogenesis-related diseases in the pathological condition, can be mainly categorized as inflammatory diseases such as arthritis, ophthalmic diseases such as diabetic retinopathy, dermatology diseases such as psoriasis and cancer, which is the most representative disease (Folkman, J. (1995) Nature Med. 1: 27-31). In particular, the primary tumor and metastatic tumors requires neovascularization for their growth (Folkman, J. (1971) New Engl. J. Med., 285: 1182-1186; Folkman, J. (1992) J. Biol. Chem. 267: 10931-10934). Of the most serious case among angiogenesis-related diseases in solid cancer, angiogenesis plays two important roles in the tumor, which are firstly to supply nutrition and oxygen necessary for growth and proliferation of tumors and secondly to promote the metastasis of cancer cells by providing the opportunity of cancer cells to enter the blood circulatory system by newborn capillaries which tumor penetrates into. Metastasis is the main cause of death in cancer patients and therefore it is important to prevent cancer metastasis after surgery or, even if when micro metastasis already occurred, to keep metastasized cancer cell in the local area so that the cancer cells do not grow longer as well as to remove completely or destroy cancer in order to improve dramatically the cure rate and survival rate of cancer. In order to completely cure cancer or avoid death, as well as even if the transition it is important to remain in the local area. Tumor cannot grow if angiogenesis activity is inhibited or removed, and the number of reports suggests that tumor angiogenesis inhibition is effective in long-term treatment of the above disease.

Also, ophthalmic diseases by angiogenesis include diabetic retinopathy which is a complication of senile macular degeneration and diabetes where the capillaries in retina invade into vitreous body, eventually leading to blindness, retinopathy of prematurity and neovascular glaucoma, from which millions of people worldwide go blind every year.

For arthritis which is caused by an autoimmune disorder, it is known that chronic inflammation of the synovial cavity induces angiogenesis during the process of the disease, in which new capillaries invade the joint, leading to the destruction of cartilage. In addition, psoriasis is a chronic proliferative disease occurring in the skin, wherein angiogenesis is bound to happen actively in order to supply large amount of blood for rapid proliferation.

Therefore, inhibition of angiogenesis may be the underlying method for treating excessive angiogenesis-related diseases such as solid cancer, ophthalmic disease, arthritis and psoriasis. However, currently used angiogenesis inhibitors are usually prepared by the method for organic synthesis, exhibiting unsatisfactory effects and have severe side effects. In particular, in the treatment of cancer, angiogenesis inhibitors targeting blood vessels supplying nutrients to the tumor without acting directly on the cancer cells are considered as one of the most promising anti-cancer treatment methods having the advantage of capability of avoiding the drug tolerance of cancer cells.

Meanwhile, benproperine whose chemical name is 1-[1-methyl-2-[2-(phenylmethyl)phenoxy]-piperidine is an available oral drug of low toxicity which has been used as an antitussive agent for cough or nonproductive cough (Yan Li, et. al., (2006) Journal of Chromatography B, 830: 71-80). However, the effect of benproperine on the metastasis of cancer cells or angiogenesis by inhibiting migration of cancer cell or endothelial cell has not been reported so far.

Hereupon, as the result of researches for substances interrupting the metastasis of cancer by inhibiting cancer cell migration and angiogenesis, the present inventors found that benproperine, which has been known only for the effect of antitussive agent and cough medicine, can effectively inhibits metastasis of cancer by interrupting cancer cell migration and inhibiting angiogenesis, and identified that benproperine can be valuably used as a novel anti-cancer drugs and further as an agent for preventing and treating angiogenesis-related diseases to complete the present invention.

SUMMARY OF THE INVENTION

The objective of the present invention is to provide a novel pharmaceutical composition for preventing and treating angiogenesis-related diseases, comprising benproperine, derivatives thereof or pharmaceutically acceptable salts thereof as an active ingredient.

Another objective of the present invention is also to provide a health functional food for preventing and improving angiogenesis-related diseases, comprising benproperine, derivatives thereof or pharmaceutically acceptable salts thereof as an active ingredient.

Another objective of the present invention is also to provide a pharmaceutical composition for inhibiting angiogenesis, comprising benproperine, derivatives thereof or pharmaceutically acceptable salts thereof as an active ingredient.

Another objective of the present invention is also to provide a pharmaceutical composition for inhibiting metastasis of cancer, comprising benproperine, derivatives thereof or pharmaceutically acceptable salts thereof as an active ingredient.

Another objective of the present invention is also to provide a method for preventing or treating angiogenesis-related disease in a subject, comprising administering benproperine derivatives or pharmaceutically acceptable salts thereof to the subject in need thereof.

Another objective of the present invention is also to provide a method for inhibiting angiogenesis in a subject, comprising administering benproperine derivatives or pharmaceutically acceptable salts thereof to the subject in need thereof.

Another objective of the present invention is also to provide a method for inhibiting metastasis of cancer in a subject, comprising administering benproperine derivatives or pharmaceutically acceptable salts thereof to the subject in need thereof.

Another objective of the present invention is also to provide a use of benproperine derivatives or pharmaceutically acceptable salts thereof, for the manufacture of a medicament for preventing or treating angiogenesis-related disease.

DETAILED DESCRIPTION OF THE PREFERRED EMBODIMENTS

For the objectives mentioned above, the present invention provides a pharmaceutical composition for preventing and treating angiogenesis-related diseases, comprising a benproperine derivative represented by Formula 1 or pharmaceutically acceptable salts thereof.

[Formula 1]

Wherein, $R_1$ and $R_2$ are independently hydrogen or hydroxyl.

As used herein, the term "benproperine derivative" refers to any compound which has a structure of Formula 1 and exhibit equal or similar levels of biological activity as benproperine.

Preferably, in benproperine derivative of Formula 1, both $R_1$ and $R_2$ are H, or $R_1$=H and $R_2$=OH, or

$R_1$=OH and $R_2$=H.

That is, benproperine derivative according to the present invention may be benproperine in Formula 2, 3-hydroxybenproperine in Formula 3, or 2-hydroxybenproperine in Formula 4.

[Formula 2]

[Formula 3]

[Formula 4]

Benproperine derivatives in Formula 1 according to the present invention can be used by preparing according to the method described in the literature or by purchasing commercially. Benproperine derivatives in Formula 1 according to the present invention can be prepared directly according to Reaction Equation 1, for example, with the reference to the method described in the literature (Yan Li, (2006) Journal of Chromatography B, 830: 71-80).

Acid addition salt is prepared in the usual way, for example, by dissolving the compound in the excessive quantity of aqueous solution of the acid followed by the precipitation of the resultant salt using water-miscible organic solvent such as methanol, ethanol, acetone, or acetonitrile. The compound of same molar amount and acid or alcohol in water (e.g., glycol monomethyl ether) can be heated and subsequently, the resultant mixture can be dried by evaporating, or precipitated salts can be filtered by suction.

Wherein, organic acid and inorganic acid can be used as free acid. Available inorganic acid may be, but is not limited to, hydrochloric acid, phosphoric acid, sulfuric acid, nitric acid and tartaric acid and available organic acid may be, but is not limited to, methanesulfonic acid, p-toluene sulfonic acid, acetic acid, tri-fluoro acetic acid, maleic acid, succinic acid, oxalic acid, benzoic acid, tartaric acid, fumaric acid, manderic acid, propionic acid, citric acid, lactic acid, glycolic acid, gluconic acid, galacturonic acid, glutamic acid, glutaric acid, glucuronic acid, aspartic acid, ascorbic acid, carbonic acid, vanillic acid, and hydroiodic acid.

Also, pharmaceutically acceptable metal salts can be prepared using base. For example, alkali metal salt or alkali earth metal salt is obtained by dissolving the compound in an excess of alkali metal hydroxide or alkali earth metal hydroxide solution, filtering the undissolved compound salt, and drying the filtrate by evaporation. Wherein, in particular but not limited to, sodium, potassium or calcium salt are pharmaceutically suitable to be prepared as metal salt. In addition, the

[Reaction Equation 1]

Wherein, $R_1$ and $R_2$ are independently hydrogen or hydroxyl.

Benproperine derivatives according to the present invention can exist in the form of pharmaceutically acceptable salts. Acid addition salt formed by pharmaceutically acceptable free acid is useful as salt. As used herein, the term "pharmaceutically acceptable salt" refers to any organic or inorganic compound addition salt whose concentration has effective action because it is relatively non-toxic and harmless to the patients and whose side effects do not degrade the beneficial efficacy of the compound which is represented by Formula 1.

corresponding silver salt can be obtained by reacting alkali metal or alkali earth metal salt with suitable silver salt (for example, silver nitrate).

Pharmaceutically acceptable salts of the compound in Formula 1 include, unless otherwise indicated, salts of acid or alkali group that may be present in the compound in Formula 1. For example, pharmaceutically acceptable salts may include sodium, calcium and potassium salts of hydroxy group and other pharmaceutically acceptable salts of amino group may include hydro-bromide, sulfate, hydrogen sulfate, phosphate, hydrogen phosphate, dihydrogen phosphate, acetate, succinate, citrate, tartrate, lactate, mandelate, methane sulfonate (mesylate) and p-toluene sulfonate (tosylate) salts and can be prepared by the preparation method for salts known in the art.

Benproperine salt in the present invention may be any pharmaceutically benproperine acceptable salt which exhibits the equivalent level of inhibitory effect against cancer cell migration and angiogenesis as benproperine, and preferably can be, but is not limited to, benproperine phosphate, sodium benproperine, potassium benproperine, and magnesium benproperine.

Benproperine according to the present invention is the nonnarcotic drug which anesthetizes specifically the stretch receptor of lung and has been used for a long time as antitussive agent and cough medicine with a confirmation of no problem in terms of safety and toxicity. The present invention, however, identifies that benproperine exhibits the inhibitory activity against cancer cell migration and angiogenesis in addition to medical use as antitussive agent and cough medicine, and proposes the novel medical use thereof as inhibitors against metastasis of cancer cell and agents for preventing and treating cancer as well as agents for preventing and treating angiogenesis-related diseases.

Specifically, in the example of the present invention, inhibitory activity against cell migration of benproperine derivatives and pharmaceutically acceptable salts thereof was analyzed using colorectal cancer cell lines in which PRL-3, cancer metastasis-related genes, is over-expressed as the subject. As a result, benproperine derivative and pharmaceutically acceptable salt thereof according to the present invention are verified to exhibit excellent inhibitory activity against cell migration by inhibiting cancer cell migration by more than 80% even at the low concentration of 5 µM (See FIGS. 3 and 4). In addition, benproperine derivatives according to the present invention exhibit an equivalent level of inhibitory activity against cell migration for a variety of cancer cell lines other than colorectal cancer cell lines (see FIG. 5).

In another example of the present invention, angiogenesis inhibitory activity of benproperine derivatives and pharmaceutically acceptable salts thereof was analyzed by in vitro endothelial morphogenesis assay using vascular endothelial cells (HUVECs, human umbilical vein endothelial cells) as the subject. As a result, benproperine derivative and pharmaceutically acceptable salt thereof according to the present invention are verified to exhibit excellent inhibitory activity against cell migration by inhibiting effectively tube formation of vascular endothelial cells even at low concentration of 10 µM (See FIG. 6).

As described in the above, benproperine, derivatives thereof and pharmaceutically acceptable salts thereof in the present invention has the activity to inhibit cancer cell migration and the angiogenesis which is crucial for the metastasis of cancer, and therefore can be valuably used not only as inhibitors of metastasis of cancer and anticancer drugs, but also as agents for preventing and treating diseases caused by excessive angiogenesis.

Therefore, the present invention provides a pharmaceutical composition for preventing or treating angiogenesis-related diseases comprising benproperine, derivatives thereof or pharmaceutically acceptable salts thereof as an active ingredient.

Within this scope, the present invention provides a pharmaceutical composition for inhibiting angiogenesis comprising benproperine, derivatives thereof or pharmaceutically acceptable salts thereof as an active ingredient.

Further, the present invention also provides a pharmaceutical composition for inhibiting metastasis of cancer comprising benproperine, derivatives thereof or pharmaceutically acceptable salts thereof as an active ingredient.

In the present invention, "prevention" refers to any act to delay or inhibit occurrence, spread or recurrence of cancer or angiogenesis-related diseases by administration of the composition of the present invention, and "treatment" refers to any act to improve or change the symptoms of the above disease for the better by administration of the composition of the present invention.

Angiogenesis, in the present invention, refers to the process by which blood vessels are newly created, in other words, the new blood vessels are generated in cells, tissues or organs, and "neovessel" refers to the newly created vessel through the process of angiogenesis. In the present invention, "angiogenesis" and "neovessel" can be written compatibly with each other. "Angiogenesis-related diseases" in the present invention refers to the diseases caused by abnormal progress of neovascularization as mentioned above.

Angiogenesis-related disease which can be prevented or treated by composition in the present invention is cancer, diabetic retinopathy, retinopathy of prematurity, corneal graft rejection, neovascular glaucoma, erythrosis, proliferative retinopathy, psoriasis, hemophilic arthropathy, capillary proliferation in atheromatous atherosclerotic plaques, keloid, wound granulation, angiostenosis, rheumatoid arthritis, osteoarthritis, autoimmune diseases, Crohn's disease, restenosis, atheromatous arteriosclerosis, stenosis of intestine, cat scratch disease, ulcers, hepatocirrhosis, glomerulonephritis, diabetic retinopathy, malignant nephrosclerosis, thrombotic microangiopathy, organ transplant rejection, glomerulopathy, diabetes, inflammation or neurodegenerative disease.

Cancers which can be prevented or treated by composition in the present invention include cervical cancer, lung cancer, pancreatic cancer, non-small-cell lung cancer, liver cancer, colon cancer, bone cancer, skin cancer, head cancer, neck cancer, skin melanoma, intraocular melanoma, uterine cancer, ovarian cancer, colorectal cancer, liver cancer, brain tumors, bladder cancer, blood cancer, gastric cancer, perianal cancer, colon cancer, breast cancer, carcinoma of the fallopian tube, uterine endometrial carcinoma, vaginal cancer, vulva carcinoma, Hodgkin's disease, esophageal cancer, small intestine cancer, endocrine adenocarcinoma, thyroid cancer, parathyroid cancer, adrenal gland cancer, soft tissue sarcoma, urethral cancer, penile cancer, prostate cancer, bladder cancer, kidney cancer, ureter cancer, renal cell carcinoma, renal pelvic carcinoma, central nervous system (CNS) tumors, primary CNS lymphoma, spinal tumors, brainstem glioma, pituitary adenoma. A pharmaceutical composition in the present invention can be valuably used for preventing and treating metastasis of cancer by inhibiting effectively cancer cell migration.

The composition in the present invention can be used in the various forms such as oral dosage forms of powders, granules, tablets, capsules, suspensions, emulsions, syrups, aerosols and injections of a sterile injectable solution formulated by the conventional method to serve the purpose of each in accordance, can be administered through various routes including oral administration or intravenous, intraperitoneal, subcutaneous, rectal and topical administration. The examples of suitable carrier, diluting agent, or diluent for example which can be included in this composition may be lactose, dextrose, sucrose, sorbitol, mannitol, xylitol, erythritol, maltitol, starch, acacia rubber, alginate, gelatin, calcium phosphate, calcium silicate, cellulose, methyl cellulose, amorphous cellulose, polyvinyl pyrrolidone, water, methyl hydroxy benzoate, propyl hydroxy benzoate, talc, magnesium stearate and mineral oil. The compositions in the present invention may further comprise fillers, anti-coagulants, lubricants, humectants, fragrances, emulsifiers, preservatives, etc.

Solid formulation agents for oral administration include tablets, pills, powders, granules, and capsules, and such solid dosage forms are formulated by mixing the composition in the present invention with one or more diluting agents, such as starch, calcium carbonate, sucrose, lactose, and gelatin. Also, lubricants such as magnesium stearate and talc can be used other than simple diluting agents.

Liquid formulation agents for oral administration can be illustrated as suspensions, solutions, emulsions, and syrups, and can include various diluting agents such as humectants, sweeteners, fragrances, and preservatives, in addition to water which is commonly used diluent and liquid paraffin.

Formulation agents for parenteral administration can be illustrated as sterile aqueous solutions, nonaqueous solvent, suspending agent, emulsion, lyophilization agent and suppository agent. Nonaqueous solvent and suspending agent may include propylene glycol, polyethylene glycol, vegetable oil such as olive oil, and injectable esters such as ethyl oleate. Injections may include conventional additives such as solvents, isotonic agent, suspending agents, emulsifiers, stabilizers, preservatives.

The composition in the present invention is administrated in a pharmaceutically effective amount. In the present invention, "pharmaceutically effective amount" refers to the amount which is applicable to the medical treatment and sufficient to treat the diseases with a reasonable benefit/risk ratio, and the level of effective amount can be determined depending on type and severity of patient's disease type, activity of the drug, sensitivity on the drug, time of administration, route of administration, discharge rate, duration of treatment, factor including other medications that are used simultaneously, and other factors well-known in the field of medicine. The composition of the present invention may be administered as individual therapy or in combination with other therapies, simultaneously with or sequentially to conventional therapies and once or multiple times. It is important to administer the minimum amount which can provide the maximum effect without the side effects Consideration of all the above factors, which can be easily determined by those skilled in the art.

Specifically, an effective amount of a compound in the composition of the present invention may vary depending on age, gender, and body weight of the patient, and 1 to 10 mg in general, or 1 to 5 mg preferably per kg of the body weight can be administered every day, every other day, or 1 to three times a day. However, the dosage may be increase or decrease depending on the route of administration, the severity of the disease, gender, body weight, age, and therefore does not in any way limit the scope of the present invention.

The composition in the present invention may be administered to the mammals such as rats, mice, cattle, and human through the various routes. All manner of administration can be expected, for example, oral administration, a job, intravenous, intramuscular, subcutaneous, and endometrial or intracerebroventricular injections may be administered by oral.

Further, the present invention also provides a method for preventing or treating angiogenesis-related disease in a subject, comprising administering a therapeutically effective amount of a benproperine derivative or pharmaceutically acceptable salts thereof to the subject in need thereof.

Within this scope, the present invention provides a method for inhibiting angiogenesis in a subject, comprising administering a therapeutically effective amount of a benproperine derivative or pharmaceutically acceptable salts thereof to the subject in need thereof.

Further, the present invention also provides a method for inhibiting metastasis of cancer in a subject, comprising administration of a therapeutically effective amount of a benproperine derivative or pharmaceutically acceptable salts thereof to the subject in need thereof.

As used herein, the term "administration" refers that the prescribed substance is provided to the patient in an appropriate manner, and the composition in the present invention can be administrated orally or parenterally through all the general routes as long as can reach the target tissue. Also, the composition in the present invention can be administered by any device that is able to deliver the active ingredients of the composition in the present invention to the target cells.

As used herein, the term "subject" refers to the animal comprising, but not limited to, human, monkey, cow, horse, sheep, pig, chicken, turkey, quail, cat, dog, mouse, rat, rabbit, or guinea pig, and refers to mammal in one example and to human in another example.

As used herein, the term "therapeutically effective amount", which is used in the combination of active ingredients, refers to the amount of benproperine, pharmaceutically acceptable salt thereof, or derivative thereof which is effective in treating or preventing the target diseases.

Pharmaceutical compositions in the present invention may include benproperine, derivative thereof, or pharmaceutically acceptable salt thereof as an active ingredient, and further comprise well-known anticancer agents or angiogenesis inhibitors, and can be used in combination with other well-known therapy for the treatment of the diseases. Other therapy includes, but is not limited to, chemotherapy, radiation therapy, hormone therapy, bone marrow transplantation, stem cell replacement therapy, other biological therapy, and immunotherapy.

Anti-cancer agent which can be included in the pharmaceutical composition in the present invention includes, not is not limited to, mechloethamine, chlorambucil, phenylalanine, mustard, cyclophosphamide, ifosfamide, carmustine (BCNU), lomustine (CCNU), streptozotocin, busulfan, thiotepa, cisplatin and carboplatin as DNA alkylating agents; dactinomycin (actinomycin D), doxorubicin (adriamycin), daunorubicin, idarubicin, mitoxantrone, plicamycin, mitomycin and C Bleomycin as anti-cancer antibiotics; and vincristine, vinblastine, paclitaxel, docetaxel, etoposide, teniposide, topotecan and iridotecan as plant alkaloids.

Angiogenesis inhibitor which can be included in the pharmaceutical composition in the present invention includes, but is not limited to, angiostatin (plsaminogen slice); anti-angiogenic antithrombin III; angiozyme; ABT-627; Bay 12-9566; benefin; bevacizumab; BMS-275291; cartilage-derived inhibitor (CDI); CAI; CD59 complement slice; CEP-7055; Col 3; combretastatin A-4; endostatin(collagen X VIII slice); fibronectin slice; Gro-beta; halofuginone; heparinase; heparin hexasaccharide slice; HMV833; human chorionic gonadotropin (hCG); IM-862; Interferon alpha/beta.gamma; interferon-inducible protein (IP-10); interleukin-12; Kringle 5 (plasminogen slice; marimastat; dexamethason; metalloproteinase inhibitor (TIMP); 2-methoxyestradiol; MMI 270 (CGS 27023A); MoAb IMC-1C11; neovastat; NM-3; Panzem; PI-88; placenta ribonuclease inhibitor; plasminogen activator inhibitor; platelet factor-4 (PF4); prinomastat; prolactin 16 kD slice; proliferin-related protein (PRP); PTK 787/ZK 222594; retinoid marimastat; squalamine; SS 3304; SU 5416; SU6668; SU11248; tetrahydrocortisol-S; tetrathiomolybdate; thalidomide; thrombospondin-1 (TSP-1); TNP-470;

transforming growth factor-beta (TGF-b); vasculostatin; vasostatin (calreticulin slice); ZD6126; ZD6474; farnesyl transferase inhibitor (FTI); and bisphosphonate (for example, alendronate, etidronate, pamidronate, risedronate, ibandronate, zoledronate, olpadronate, icandronate or neridronate).

The present invention also provides health functional food for preventing or improving angiogenesis-related diseases comprising a benproperine derivative or pharmaceutically acceptable salts thereof as an active ingredient.

The composition, in the present invention, comprising benproperine, derivative thereof or pharmaceutically acceptable salt thereof can be used variously in drug, food and beverage, etc., which is effective in preventing and improving angiogenesis-related diseases. The food in which benproperine and pharmaceutically acceptable salt thereof are added includes various kinds of food, beverage, chewing gum, tea, vitamin complex, health supplementary food and can be used as a form of powder, granule, tablet, capsule, or drink.

Benproperine, derivative thereof or pharmaceutically acceptable salt thereof in the present invention has been confirmed to have no problem in terms of stability, toxicity and side effect while used for a long time as antitussive agent and cough medicine in the art, and therefore drug that can be used with confidence even when taken for a long time for the purpose of preventing an improving the disease.

Benproperine, derivative thereof or pharmaceutically acceptable salt thereof in the present invention can be added in the food or beverage for the purpose of preventing and improving angiogenesis-related diseases. Wherein, the amount thereof in the food or beverage can be generally 0.01 to 15 weight % of total food weight, 0.02 to 10 g, or preferably 0.3 to 1 g based on the 100 Ml of health beverage composition.

Health functional food in the present invention can contain not only the above compounds as essential ingredients in the indicated proportion but also sitologically acceptable food supplementary additives, such as various flavoring agents and natural carbohydrates as additional ingredients. The example of the aforementioned natural carbohydrate is usual sugar such as monosaccharide such as glucose and fructose, disaccharide such as maltose and sucrose and polysaccharide such as dextrin and cyclodextrin, and sugar alcohol such as xylitol, sorbitol and erythritol. Other than the aforementioned flavoring agent, natural flavoring agent (thaumatin, sevita extract (for example, rebaudioside A, glycyrrhizin, etc.)) and synthetic flavoring agent (saccharin, aspartame, etc.) can be favorably used as a flavoring agent. The proportion of the above natural carbohydrate is typically about 1 to 20 g, or preferably about 5 to 12 g per 100 ml of health functional food in the present invention. Health functional food in the present invention may contain, in addition to the above, various nutritional supplements, vitamins, minerals (electrolytes), flavoring agents such as natural flavoring agents and synthetic flavoring agents, colorants and weighting agents (cheese, chocolate, etc.), pectic acid and salts thereof, alginic acid and salts thereof, organic acid, protective colloid thickener, pH control agents, stabilizers, preservatives, glycerin, alcohol, carbonization agent used in carbonated beverage. In addition, health functional food in the present invention may include pulp for preparing natural fruit juices, fruit juice beverage and vegetable beverage. These components can be used independently or in combination. The proportion of these additives is not so important, but is selected typically in the range of 0 to 20 per 100 of the composition of the present invention by weight.

The present invention is described in more details through providing Examples as below. However, these Examples are merely meant to illustrate, but in no way to limit, the claimed invention.

REFERENCE EXAMPLE 1

Preparation of Benproperine Derivative

Benproperine derivatives in Formulas 2 to 4 was prepared according to the Reaction Equation 1 with the reference to the method described in the literature (Yan Li, et. al. (2006) Journal of Chromatography B, 830: 71-80).

[Reaction Equation 1]

I

Wherein, $R_1$ and $R_2$ are independently hydrogen or hydroxyl.

$^1$H-NMR analysis results of benproperine derivatives prepared as the above are as follows.

Benproperine in Formula 2

$^1$H NMR (CDCl$_3$): 7.23(6H,m), 7.09(1H,d,J=6.6), 6.86 (2H,t,8.1), 4.07(1H,m), 3.98(2H,s), 3.85(1H,m), 2.97(1H,m), 2.54(4H,m), 1.55(4H,m), 1.42(2H,m), 1.11(3H, d,J=6.6).

3-hydroxybenproperine in Formula 3

$^1$H-NMR (CDCl$_3$): 7.28(7H, m), 6.85(2H, m), 4.12(1H, m), 4.01(2H, m), 3.85(2H, m), 3.68(5H, m), 2.57(4H, m), 1.21(3H, m).

2-hydroxybenproperine in Formula 4

$^1$H-NMR (CDCl$_3$): 7.3(1H, m), 7.18(1H, m), 7.04(2H, m), 6.93(2H, m), 6.80(2H, m), 4.09(1H, m), 4.01(2H, d, J=8.76), 3.89(2H, d, J=8.79), 2.71(5H, m), 1.7(5H, m), 1.17(3H, d, J=3.3).

Figure 1:
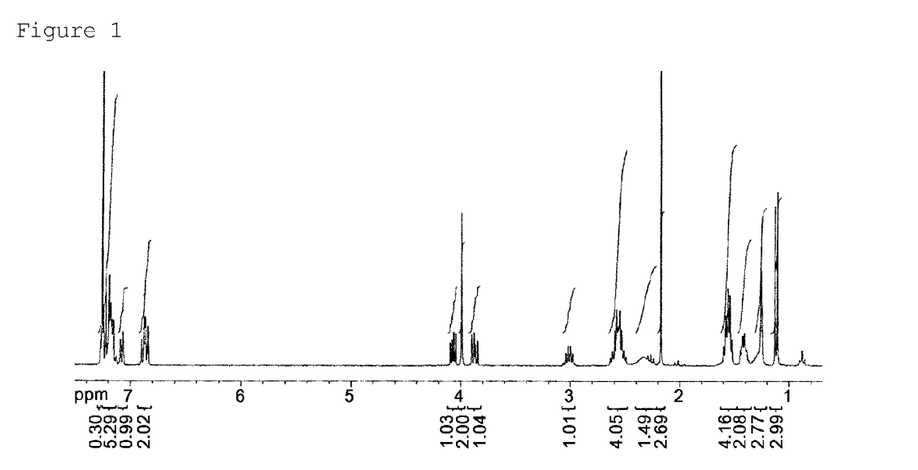
FIG. 1 shows the analysis result of benproperine in Formula 2 according to the present invention with $^1$H-NMR.

FIG. 1 shows $^1$H-NMR analysis spectrum of benproperine in Formula 2.

EXAMPLE 1

Analysis of Cytotoxicity of Benproperine

In order to examine the cytotoxicity of the benproperine derivative prepared in Reference Example 1, after DLD-1 cell (ATCC-CCL-221), which is the human colorectal cancer cell lines in which PRL-3 cancer metastasis-related genes is over-expressed, was cultured in the RPMI culture medium containing 10% fetal bovine serum (FBS) and maintained at 37° C., 5% $CO_2$, the cell was detached using 0.05% trypsin-EDTA. $4 \times 10^3$ cells which were calculated by hemocytometer were inoculated in each well of 96-well plates medium containing 10% FBS, and cultured in 37° C. incubator containing 5% $CO_2$. After 24 hours, the culture medium of each well was replaced with new medium containing control (0.1% DMSO) and benproperine in Formula 2, which was prepared in Reference Example 1, by concentration (5 to 10 μM) and replace it with a new medium, and was cultured in 37° C., 5% $CO_2$ incubator for 48 hours. After WST-1 (Roche) of 10 μl was added in each well of the above plate followed by 2 hours of culture, absorbance was measured at 450 nm using ELISA reader (Bio-Rad).

Figure 2:
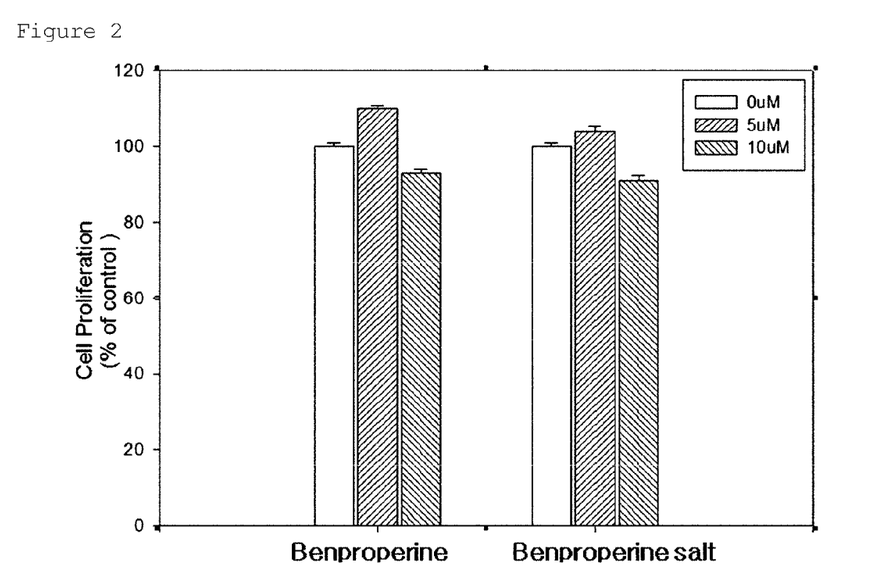
FIG. 2 shows the measurement result of cytotoxicity of benproperine derivative according to the present invention.

As the result shown in FIG. 2, benproperine according to the present invention exhibits no cytotoxicity even at the concentration of 10 μM.

EXAMPLE 2

Analysis of in vitro Cell Migration

In order to analyze inhibitory activity against in vitro cell migration of the benproperine derivative according to the present invention, after DLD-1 cell (ATCC-CCL-221), which is the human colorectal cancer cell lines in which PRL-3, cancer metastasis-related genes, is over-expressed, was grown around by 90% on the culture plate containing RPMI medium, the medium was removed and the cell was washed with PBS. The washed cell was processed with trypsin-EDTA, cultured $CO_2$ incubator at 37° C. for 15 hours, and then detached. The resultant cells in which 10% FBS-containing RPMI medium was added were collected in the falcon tube and the medium was removed by centrifugation. The process in which FBS-free RPMI medium were added in the obtained cells and the medium was removed by centrifugation was repeated twice. After the obtained cells in which FBS-free RPMI medium was added were suspended, the number of cells was counted using a hemocytometer.

The cells of $8 \times 10^4$ cells/200 μl were added to trans-wells which were placed on 24-well plates. FBS-free RPMI medium of 500 μl was added using the empty space where trans-wells were placed on well plates and cultured in a $CO_2$ incubator at 37° C. for 12 to 16 hours. After the medium has been removed by placing trans-wells upside down on hand towel following culture, crystal violet of 500 μl (20% MeOH in 5 mg/ml) was added to each well of 24-well plates and trans-wells were put in a $CO_2$ incubator for 30 minutes. Stained trans-wells were washed with PBS and placed upside down on hand towel so that the remaining solution was impregnated. Membrane was placed on the cover slip with the side where the cells didn't move facing upwards and wiped well with a cotton swab. The cover slip on whose edges nail polish was applied a little was put on a slide glass and fixed. The prepared sample was photographed with an inverted microscope (TE 300, Nikon, Japan) equipped with digital camera and the number of cells having moved was counted.

Inhibitory activity against cell migration of benproperine and pharmaceutically acceptable salt thereof in Formulas 2 to 4 according to the present invention was observed by the above method, and inhibition rate was calculated by the Mathematical Equation 1.

$$\text{Inhibition rate of cell migration}(\%) = 100 - \left[ \frac{\text{Cell migration number in treated sample}}{\text{Cell migration number in control sample}} \times 100 \right]$$

[Mathematical Equation 1]

Wherein the control sample was observed by adding 0.1% dimethyl sulfoxide (DMSO) only without addition of the compound in the present invention.

Figure 3:
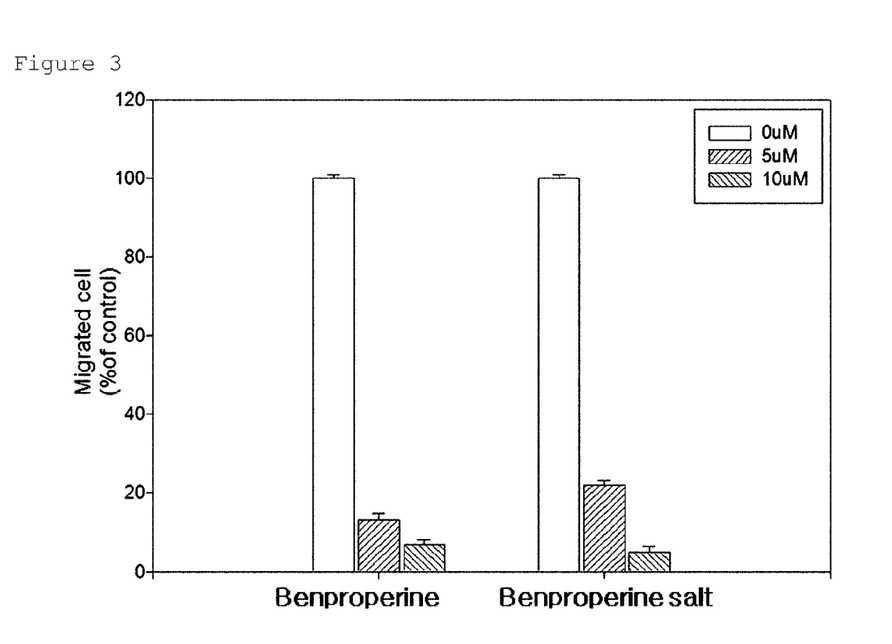
FIG. 3 shows the analysis result of inhibitory activity against cell migration of benproperine derivative and pharmaceutically acceptable salt thereof according to the present invention.

As the result represented in FIG. 3, benproperine in Formula 2 according to the present invention and phosphate salt thereof were verified to inhibit the migration of colorectal cancer cell more than 80% at concentration of 5 μM and nearly more than 90% at concentration of 10 μM compared to the control sample.

Figure 4:
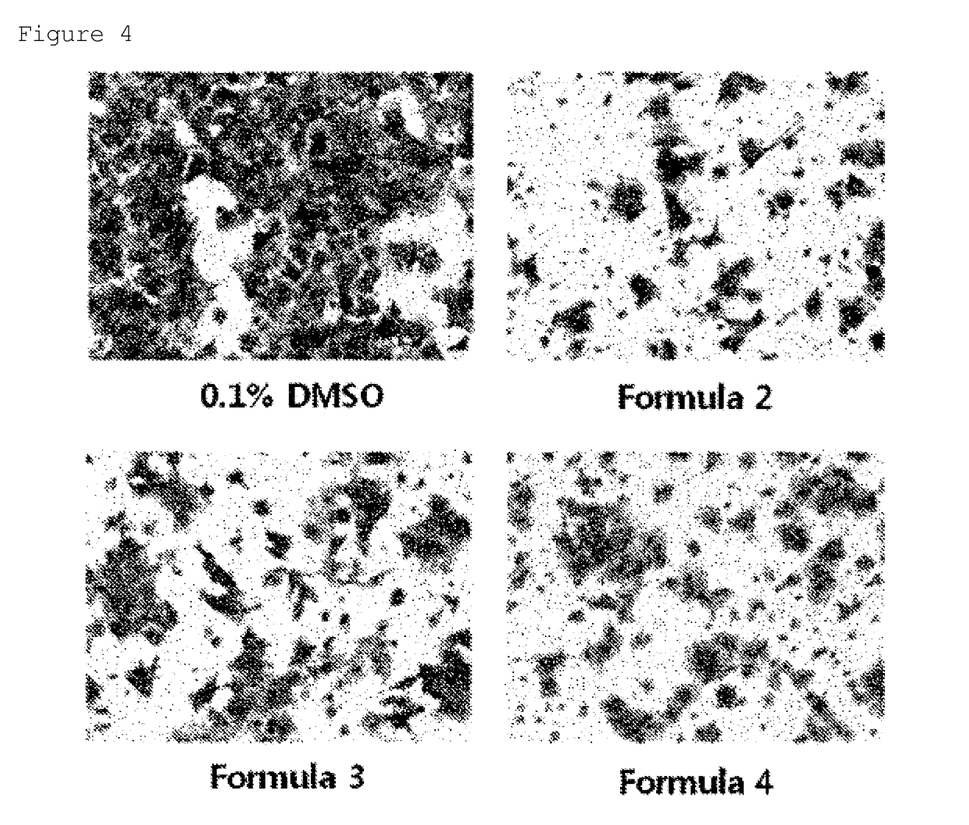
FIG. 4 shows the analysis result of inhibitory activity against cell migration of benproperine derivative, which is represented by Formulas 2 to 4, according to the present invention.

FIG. 4 shows the analysis result of inhibitory activity against cell migration for colorectal cancer cell line of benproperine in Formula 2, 3-hydroxybenproperine in Formula 3, and 2-hydrorxybenproperine in Formula 2 according to the present invention. As represented in FIG. 4, all the benproperine derivatives in Formulas 2 to 4 according to the present invention can be seen to inhibit effectively the migration of colorectal cancer cell compared with control sample of 0.1% DMSO.

Figure 5:
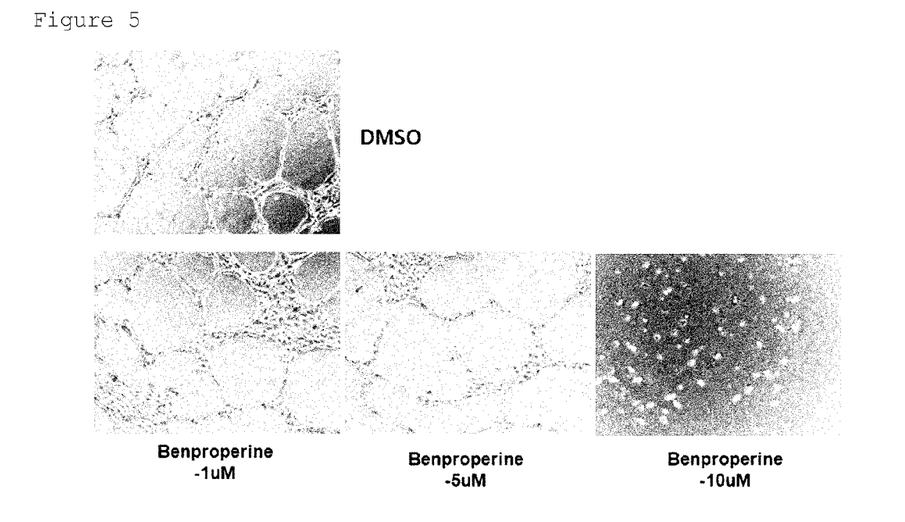
FIG. 5 shows the analysis result of inhibitory activity against cell migration for various human solid cancer cells of benproperine derivative according to the present invention.

In addition, the analysis result of inhibitory activity against cell migration of benproperine according to the present invention with pancreatic cancer cell line AsPc-1 cells (ATCC-CRL-1682), melanoma cell line B16F10 (ATCC-CRL-6475) and breast cancer cell line A375P (KCLB-80003) cells besides colorectal cancer cell line DLD-1 cells as the subjects, as represented in FIG. 5, verified that the cell migration of all the cancer cell lines are prominently inhibited by treating with benproperine of 10 μM compared with DMSO-treated contrast sample.

EXAMPLE 3

Analysis of Inhibitory Activity Against Angiogenesis Using in vitro Endothelial Morphogenesis Assay Inhibitory activity against angiogenesis of benproperine according to the present invention was observed with vascular endothelial cell HUVECs (Human Umbillical Vein Endothelial Cells), which is human cell line, under in vivo-like condition, using in vitro endothelial morphogenesis assay.

Specifically, HUVECs (ATCC-CRL-2873) was brought into the starvation state by culturing in a serum-free medium overnight. Matrigel matrix (BD biosciences) of 0.2 ml was added in each well of 24-well plates and placed in the 37° C. incubator for 1 hour to coat the surface of well. 0.2 ml $2 \times 10^4$ cells prepared in the above were added to each well coated with Matrigel matrix and cultured in a $CO_2$ incubator for 30 minutes. After culture, fresh medium containing benproperine of 1, 5, and 10 μM concentration was added in each well followed by the addition of 1% serum and cultured in a $CO_2$ incubator for 24 hours. After culture, the degree of inhibitory activity against HUVECs tube formation of benproperine was observed under a microscope.

Figure 6:
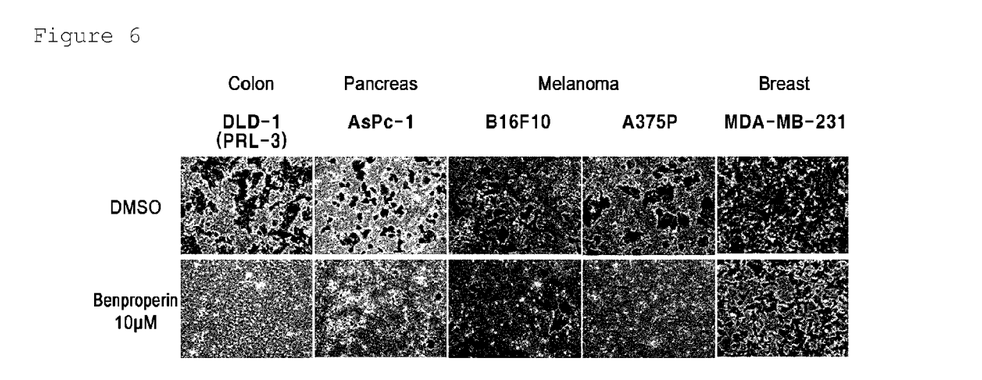
FIG. 6 shows the analysis result of inhibitory activity against angiogenesis for vascular endothelial cell (HUVEC) of benproperine derivative according to the present invention.

As a result represented in FIG. 6, benproperine in the present invention was verified to have excellent inhibitory activity against angiogenesis by inhibiting the tube formation of HUVECs in a concentration-dependent manner, in particular, significantly at a concentration of 10 μM compared to the DMSO-treated control group.

EXAMPLE 4

Analysis of Inhibitory Activity Against in vivo Metastasis of Cancer

In order to analyze inhibitory activity against in vivo cell migration of benproperine according to the present invention, inhibitory activity against metastasis of cancer of benproperine was analyzed using tumor model where melanoma cells are transplanted.

Specifically, B16F10 human melanoma cell line (ATCC-CRL-6475) was inoculated to DMEM (GIBCO, USA) medium containing 10% FBS (GIBCO, USA), and cultured at 5% $CO_2$, 37° C. 7-week-old female specific pathogen free (SPF) C57BL/6 mouse was adapted to the laboratory environment by supplying enough antibiotic-free pellet feed (Samyang feed Inc., South Korea) and sterilized tap water, and then used in the experiment.

Cultured B16F10 human melanoma cells were suspended in PBS 200 μl at the concentration of $2 \times 10^6$ cells/ml, and inoculated subcutaneously to tail vein of the above mouse using a 26 gauge needle. After 3 hours of inoculation, the mice were divided into two groups in which the control group treated with sterile distilled water and the experimental group was intraperitoneally administered with benproperine of 50 mg/kg once a day, 14 times in total. The administration continued for 13 consecutive days, and then stopped. On day after the administration, autopsy was performed to the mouse of each group to extract the lung, and the number of colonies of metastasized cancer cells (melanoma cells) was counted.

TABLE 1

| Group | Dose (mg/kg) | Number of lung colony (average ± SD) | Inhibition rate (%) |
| --- | --- | --- | --- |
| Negative control group | 0 | 106 ± 23.3 | |
| Benproperine treated group | 50 | 58.2 ± 25.8 | 45.1* |

*Significance t-test: p < 0.001

As a result, represented in Table 1, it was verified that while in mice which were treated with sterile distilled water (control group), melanoma cells metastasized to the lungs and formation of numerous colonies was observed, in mice which were administered with benproperine, the number of colonies generated by metastasis of melanoma cells was significantly decreased. The result indicates that treatment with benproperine according to the present invention can inhibit the metastasis of cancer cell by 45.1% compared with the control group.

EXAMPLE 5

Acute Toxicity Experiment of Oral Administration to Rats

In order to identify the toxicity of benproperine and pharmaceutically acceptable salt thereof according to the present invention, acute toxicity experiment was performed with laboratory animal as the subject as follow.

After 6-week-old specific pathogen free (SPF) SD bred rats were divided into groups of 2 specimens, and were orally administered once with benproperine which was prepared in Reference Example 1 and dissolved in injectable distilled water with a dose of 1000 mg/kg. Death, clinical symptoms, weight changes of the animals after the administration of the test substance were observed, and hematological examination and biochemical examination of blood were conducted, the abnormality of thoracic cavity organs and abdominal cavity organs was observed with naked eye following autopsy.

As a result, clinical symptoms worth of special mention, death, or weight changes were not observed in all animals that were administered with the test substance, and hematological examination, biochemical examination of blood, and autopsy showed no toxic change.

Benproperine and pharmaceutically acceptable salt thereof according to the present invention, therefore, were judged as safe substances whose minimum lethal dose (LD50) for oral administration is greater than 1000 mg/kg since all the rats showed no toxic change to 1000 mg/kg.

EXAMPLE 6

Analysis of in vivo Inhibitory Activity of the Salt of Benproperine against Metastasis of Cancer In order to examine the in vivo inhibitory activity of the salt of benproperine of the present invention against metastasis of cancer, the inhibitory activity of benproperine phosphate (MD-164) against metastasis of cancer and toxicity of the same were examined by using the animal model which was transplanted with human-derived pancreatic cancer cell line (AsPC-1) in caudal vein.

To be specific, the human-derived pancreatic cancer cell line AsPC-1 (adenocarcinoma; Pancrease cancer) had been stored frozen in liquid nitrogen and it was thawed and cultured in $CO_2$ incubator (Form a, USA) with 5% $CO_2$ at 37° C. Specific-pathogen-free (SPF) BALB/C nude mouse (orient, Korea) was used in this experiment.

The cultured cells were collected and diluted to a cell concentration of $5 \times 10^6$ cells/ml by adding serum free media. Then, the animal model was prepared by intravenous administration of 0.2 ml of the cell culture to each mouse. Subsequently, 5 mg/ml of benproperine phosphate (MD-164)

(KRIBB, Korea) was prepared by dissolving it in 0.5% Tween80 and orally administered to the mouse at a dose of 10 ml/kg five times a week, for a total of 20 times.

Figure 7:
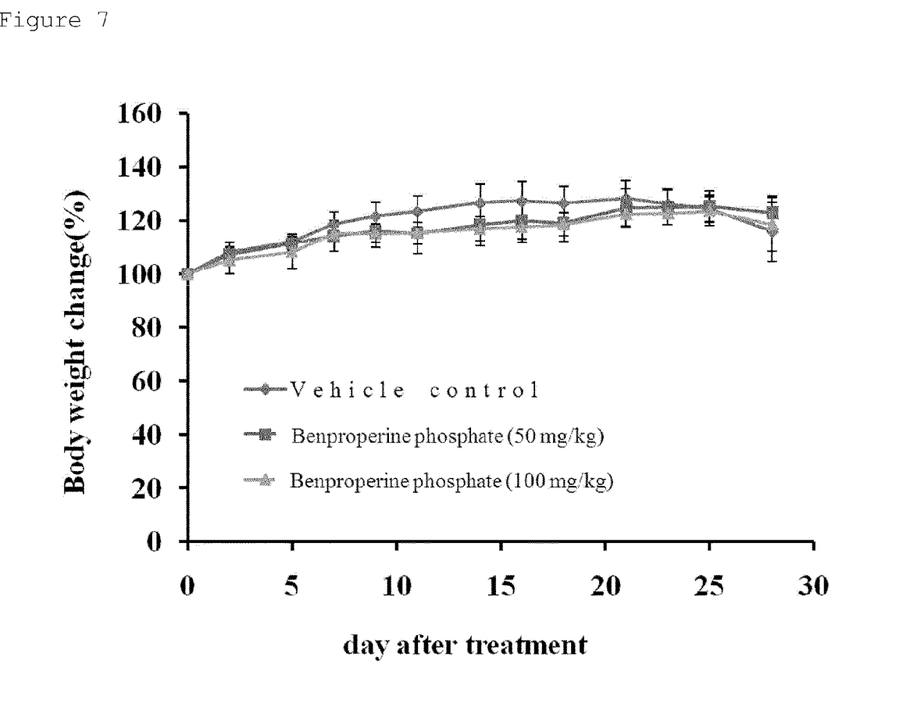
FIG. 7 shows the analysis result on the weight change with regard to the administration of benproperine phosphate of the present invention.

First, in order to analyze the toxicity of benproperine phosphate, the weight of all test groups was measured prior to administration of the compound, three times a week during the test period. As a result, there was no significant weight loss observed even when benproperine phosphate was administered at a dose of 50 and 100 mg/kg, in comparison to a control group (FIG. 7). FIG. 7 shows the analysis result on the weight change with regard to the administration of benproperine phosphate of the present invention. These results suggest that benproperine phosphate is not toxic in the subject.

Secondly, in order to establish an animal model of pulmonary metastases, luciferase stably expressing AsPC-1 cell line was transplanted into a tail vein of mouse at a dose of $1 \times 10^6$ cells/mouse. Successful transplantation of cancer cell was examined through non-invasive bioluminescence imaging. The 15 mg/ml of luciferin in PBS was injected to both sides of abdominal site of mouse at a volume of 50 µl each. After 5 minutes of injection, imaging of the animal model was done for 5 minutes by using a live animal imaging system (PHOTONE IMAGER, Biospace) set in bioluminescence counting mode. After 28 days of drug administration, the rate of metastasis of cancer calls was examined by bioluminescence imaging. Bioluminescence imaging results were examined by using M3 vision 6.620 of Biospacelab. The bioluminescence value was measured for equal area of each mouse subject, and the metastasis inhibition rate (%) in the group administered with benproperine phosphate was determined compared to a control group by the Mathematical Equation 2.

[Mathematical Equation 2]

$$\text{Metastasis inhibition rate (\%)} = 100 - \left[ \frac{\text{bioluminescence in treated group}}{\text{bioluminescence in control group}} \times 100 \right]$$

Figure 8:
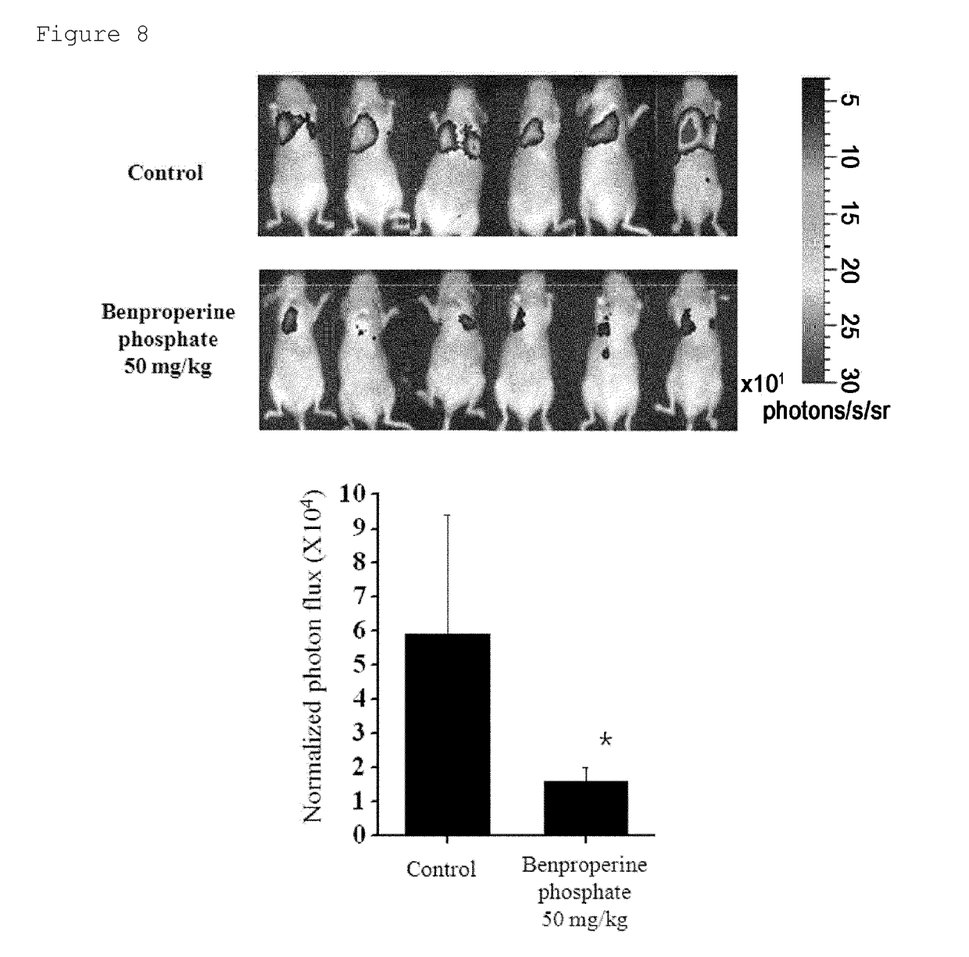
FIG. 8 shows the examination results on the metastatic activity of cancer cell after the administration of benproperine phosphate of the present invention.

On the 28th day after drug administration, the lung of animal model was collected, the number of colony was measured, and imaging signal (photone/s/sr) was also measured. As a result, the group administered with benproperine phosphate at a dose of 50 mg/kg showed 71.5% inhibition rate against metastasis compared to a control group (FIG. 8). FIG. 8 shows the examination results on the metastatic activity of cancer cell after the administration of benproperine phosphate of the present invention. These results suggest that benproperine phosphate has an inhibitory activity against the metastasis of cancer cells.

PREPARATION EXAMPLE 1

Preparation of Powders

| | |
|---|---|
| Benproperine, derivative thereof, pharmaceutically acceptable salt thereof | 20 mg |
| Lactose | 100 mg |
| Talc | 10 mg |

Powders were prepared by mixing the above ingredients followed by filling in airtight packs according to the usual method for preparing powders.

PREPARATION EXAMPLE 2

Preparation of Tablet

| | |
|---|---|
| Benproperine, derivative thereof, pharmaceutically acceptable salt thereof | 10 mg |
| Corn starch | 100 mg |
| Lactose | 100 mg |
| Magnesium stearate | 2 mg |

Tablet was prepared by mixing the above ingredients followed by compressing according to the usual method for preparing tablet.

PREPARATION EXAMPLE 3

Preparation of Capsule

| | |
|---|---|
| Benproperine, derivative thereof, pharmaceutically acceptable salt thereof | 10 mg |
| Crystalline cellulose | 3 mg |
| Lactose | 14.8 mg |
| Magnesium stearate | 0.2 mg |

Capsule was prepared by mixing the above ingredients followed by filling in gelatin capsule according to the usual method for preparing capsule.

PREPARATION EXAMPLE 4

Preparation of Injection

| | |
|---|---|
| Benproperine, derivative thereof, pharmaceutically acceptable salt thereof | 10 mg |
| Mannitol | 180 mg |
| Injectable sterile distilled water | 2974 mg |
| $Na_2HPO_4 12H_2O$ | 26 mg |

Injection was prepared by mixing the above ingredients in sterile distilled water so that the amount of ingredient per ampule (2 ml) may be as above according to the usual method for preparing injection.

PREPARATION EXAMPLE 5

Preparation of Liquid Agent

| | |
|---|---|
| Benproperine, derivative thereof, pharmaceutically acceptable salt thereof | 10 mg |
| Isomerized sugar | 10 g |
| Mannitol | 5 g |
| Purified water | Suitable quantity |

Liquid agent was prepared by mixing the above ingredients in purified water followed by adding purified water to adjust the total volume to 100 ml and sterilizing following filling in brown bottle according to the conventional method for preparing liquid agent.

PREPARATION EXAMPLE 6

Preparation of Health Food

| | |
|---|---|
| Benproperine, derivative thereof, pharmaceutically acceptable salt thereof | 10 mg |
| Vitamin compound | Suitable quantity |
| Vitamin A Acetate | 70 µg |
| Vitamin E | 1.0 mg |
| Vitamin B1 | 0.13 mg |
| Vitamin B2 | 0.15 mg |
| Vitamin B6 | 0.5 mg |
| Vitamin B12 | 0.2 µg |
| Vitamin C | 10 mg |
| Biotin | 10 µg |
| Nicotinamide | 1.7 mg |
| Folic Acid | 50 µg |
| Calcium pentothenate | 0.5 mg |
| Mineral mixture | Suitable quantity |
| Ferrous sulfate | 1.75 mg |
| Zinc Oxide | 0.82 mg |
| Magnesium carbonate | 25.3 mg |
| Mono Potassium phosphate | 15 mg |
| Di Potassium phosphate | 55 mg |
| Potassium citrate | 90 mg |
| Calcium carbonate | 100 mg |
| Magnesium Chloride | 24.8 mg |

After powders were prepared by mixing the above ingredients, the resultant powders can be used in preparing the heath food composition according to the usual method for preparing health food.

The composition ratio of vitamin and mineral complex in the above is to mix the ingredients which are relatively appropriate for health food as the example; on of the mixture of the above, the mixing ratio can be changed arbitrarily.

PREPARATION EXAMPLE 7

Preparation of Health Beverage

| | |
|---|---|
| Benproperine, derivative thereof, pharmaceutically acceptable salt thereof | 10 mg |
| Vitamin C | 15 g |
| Vitamin E (Powder) | 100 g |
| Ferrous Lactate | 19.75 g |
| Zinc Oxide | 3.5 g |
| Nicotinamide | 3.5 g |
| Vitamin A | 0.2 g |
| Vitamin B1 | 0.25 g |
| Vitamin B2 | 0.3 g |
| Water | Suitable quantity |

After above ingredients were mixed and heated at 85° C. about for 1 hour with stirring, the prepared solution was put into the sterilized container of 2 l following filtration according to the conventional method for preparing health beverage. The container was sealed, sterilized, refrigerated, and then used for preparing the composition of health beverage.

The composition ratio in the above is to mix the ingredients which are relatively appropriate for beverage as the example; on of the mixture of the above, the mixing ratio can be changed arbitrarily depending on regional and national preference such as consumer class, consumer country, and uses.

Effect of the Invention

As described in the above, benproperine, derivative thereof and pharmaceutically acceptable salt thereof according to the present invention can be valuably used as anticancer agents, inhibitors of metastasis of cancer and agents for preventing and treating angiogenesis-related diseases by inhibiting cancer cell migration and the angiogenesis which is crucial for the metastasis of cancer.

What is claimed is:

1. A method for inhibiting metastasis of cancer in a subject, comprising administering a therapeutically effective amount of a benproperine derivative represented by Formula 1 or pharmaceutically acceptable salts thereof to the subject in need of the same

[Formula 1]

wherein $R_1$ and $R_2$ are independently hydrogen or hydroxyl.

2. The method according to claim 1, wherein the benproperine derivative is selected from the group consisting of benproperine represented by Formula 2, 3-hydroxybenproperine represented by Formula 3, and 2-hydroxybenproperine represented by Formula 4

[Formula 2]

[Formula 3]

3. The method according to claim 1, wherein the pharmaceutically acceptable salt of benproperine derivative is selected from the group consisting of benproperine phosphate, sodium benproperine, potassium benproperine and magnesium benproperine.

4. The method according to claim 1, wherein the cancer is cervical cancer, lung cancer, pancreatic cancer, non-small-cell lung cancer, liver cancer, colon cancer, bone cancer, skin cancer, head cancer, neck cancer, skin melanoma, intraocular melanoma, uterine cancer, ovarian cancer, colorectal cancer, liver cancer, brain tumors, bladder cancer, blood cancer, gastric cancer, perianal cancer, colon cancer, breast cancer, carcinoma of the fallopian tube, uterine endometrial carcinoma, vaginal cancer, vulva carcinoma, Hodgkin's disease, esophageal cancer, small intestine cancer, endocrine adenocarcinoma, thyroid cancer, parathyroid cancer, adrenal gland cancer, soft tissue sarcoma, urethral cancer, penile cancer, prostate cancer, bladder cancer, kidney cancer, ureter cancer, renal cell carcinoma, renal pelvic carcinoma, central nervous system (CNS) tumors, primary CNS lymphoma, spinal tumors, brainstem glioma or pituitary adenoma.

5. The method according to claim 1, further comprising administering anti-cancer agents to the subject.

6. The method according to claim 5, the anti-cancer agents are one or more selected from the group consisting of DNA alkylating agents, anti-cancer antibiotics and plant alkaloids.

7. The method according to claim 1, further comprising administering angiogenesis inhibitor to the subject.

8. A method for treating angiogenesis-related disease in a subject, comprising administering a therapeutically effective amount of a benproperine derivative represented by Formula 1 or pharmaceutically acceptable salts thereof to the subject in need thereof wherein $R_1$ and $R_2$ are independently hydrogen or hydroxyl.

9. The method according to claim 8, wherein the benproperine derivative is selected from the group consisting of benproperine represented by Formula 2, 3-hydroxybenproperine represented by Formula 3, and 2-hydroxybenproperine represented by Formula 4

10. The method according to claim 8, wherein the pharmaceutically acceptable salt of benproperine derivative is selected from the group consisting of benproperine phosphate, sodium benproperine, potassium benproperine and magnesium benproperine.

11. The method according to claim 8, wherein the angiogenesis-related disease is cancer, diabetic retinopathy, retinopathy of prematurity, corneal graft rejection, neovascular glaucoma, erythrosis, proliferative retinopathy, psoriasis, hemophilic arthropathy, capillariy proliferation in atheromatous atherosclerotic plaques, keloid, wound granulation, angiostenosis, rheumatoid arthritis, osteoarthritis, autoimmune diseases, Crohn's disease, restenosis, atheromatous arteriosclerosis, stenosis of intestine, cat scratch disease, ulcers, hepatocirrhosis, glomerulonephritis, diabetic retinopathy, malignant nephrosclerosis, thrombotic microangiopathy, organ transplant rejection, glomerulopathy, diabetes, inflammation or neurodegenerative disease.

12. The method according to claim 11, wherein the cancer is cervical cancer, lung cancer, pancreatic cancer, non-small-cell lung cancer, liver cancer, colon cancer, bone cancer, skin cancer, head cancer, neck cancer, skin melanoma, intraocular melanoma, uterine cancer, ovarian cancer, colorectal cancer, liver cancer, brain tumors, bladder cancer, blood cancer, gastric cancer, perianal cancer, colon cancer, breast cancer, carcinoma of the fallopian tube, uterine endometrial carcinoma, vaginal cancer, vulva carcinoma, Hodgkin's disease, esophageal cancer, small intestine cancer, endocrine adenocarcinoma, thyroid cancer, parathyroid cancer, adrenal gland cancer, soft tissue sarcoma, urethral cancer, penile cancer, prostate cancer, bladder cancer, kidney cancer, ureter cancer, renal cell carcinoma, renal pelvic carcinoma, central nervous system (CNS) tumors, primary CNS lymphoma, spinal tumors, brainstem glioma or pituitary adenoma.

13. The method according to claim 8, further comprising administering anti-cancer agents to the subject.

14. The method according to claim 13, the anti-cancer agents are one or more selected from the group consisting of DNA alkylating agents, anti-cancer antibiotics and plant alkaloids.

15. The method according to claim 14, further comprising administering angiogenesis inhibitor to the subject.

16. A method for inhibiting angiogenesis in a subject, comprising administering a therapeutically effective amount of a benproperine derivative represented by Formula 1 or pharmaceutically acceptable salts thereof to the subject in need of the same

[Formula 1]

wherein $R_1$ and $R_2$ are independently hydrogen or hydroxyl.

* * * * *